United States Patent
Kubota et al.

(10) Patent No.: US 8,104,349 B2
(45) Date of Patent: Jan. 31, 2012

(54) FLAW DETECTION TRACKING DEVICE FOR PIPE OR TUBE AND AUTOMATIC FLAW DETECTING APPARATUS FOR PIPE OR TUBE USING THE SAME

(75) Inventors: Hiroshi Kubota, Osaka (JP); Yoshiyuki Nakao, Osaka (JP); Masami Ikeda, Osaka (JP); Nobuyuki Mori, Osaka (JP); Hiroshi Sato, Fujisawa (JP)

(73) Assignee: Sumitomo Metal Industries, Ltd., Osaka (JP)

( * ) Notice: Subject to any disclaimer, the term of this patent is extended or adjusted under 35 U.S.C. 154(b) by 179 days.

(21) Appl. No.: 12/312,962

(22) PCT Filed: Oct. 26, 2007

(86) PCT No.: PCT/JP2007/070890
§ 371 (c)(1),
(2), (4) Date: Feb. 9, 2010

(87) PCT Pub. No.: WO2008/068972
PCT Pub. Date: Jun. 12, 2008

(65) Prior Publication Data
US 2010/0126278 A1 May 27, 2010

(30) Foreign Application Priority Data
Dec. 4, 2006 (JP) ................................. 2006-326817

(51) Int. Cl.
*G01N 29/04* (2006.01)
*G01N 27/82* (2006.01)
*G01B 5/28* (2006.01)
(52) U.S. Cl. ................................ 73/618; 73/622; 702/39

(58) Field of Classification Search .................... 73/618, 73/596, 597, 598, 600, 602, 622; 702/39; 324/220
See application file for complete search history.

(56) References Cited

U.S. PATENT DOCUMENTS

| 3,084,541 A | * | 4/1963 | Rouge | 73/862 |
| 3,479,743 A | * | 11/1969 | Zemberry | 33/836 |
| 4,710,712 A | * | 12/1987 | Bradfield et al. | 324/227 |

(Continued)

FOREIGN PATENT DOCUMENTS

GB 2456831 * 7/2011

(Continued)

*Primary Examiner* — J M Saint Surin
(74) *Attorney, Agent, or Firm* — Clark & Brody

(57) ABSTRACT

A tracking device is provided with a non-contact type displacement gauge, a positioner which moves a flaw detecting sensor within a plane perpendicular to an axial direction of a pipe or tube, and a positioning controller which controls the positioner. The positioning controller predicts a time until a portion of the pipe or tube whose displacement is measured by the displacement gauge reaches a predetermined position on a straight line extending in a Z-axis direction through a rotational center of the pipe or tube on the basis of the positional relationship between the displacement gauge and the flaw detecting sensor and a rotational speed of the pipe or tube; controls the positioner on the basis of the displacement measured by the displacement gauge and an operational delay time of the positioner in such a manner that the relative position of the flaw detecting sensor to the pipe or tube after the lapse of the predicted time becomes substantially constant in the Z-axis direction; and moves the flaw detecting sensor along the Z-axis direction. The positioning controller performs the same control in an X-axis direction.

7 Claims, 6 Drawing Sheets

U.S. PATENT DOCUMENTS 7,997,139 B2 * 8/2011 Owens et al. .................. 73/622
2009/0217763 A1 * 9/2009 Yamano .......................... 73/622

FOREIGN PATENT DOCUMENTS

| JP | 59-3347 | 1/1984 |
| JP | 59-29156 | 2/1984 |
| JP | 60-224060 | 11/1985 |
| JP | 61-56963 | 3/1986 |
| JP | 64-38648 | 2/1989 |
| JP | 2-59658 | 2/1990 |
| JP | 4-66896 | 3/1992 |
| JP | 4-29411 | 7/1992 |
| JP | 5-265559 | 10/1993 |
| JP | 2006-105892 | 4/2006 |
| WO | 2007/024000 | 3/2007 |

\* cited by examiner

Information from high-order process computer

FLAW DETECTION TRACKING DEVICE FOR PIPE OR TUBE AND AUTOMATIC FLAW DETECTING APPARATUS FOR PIPE OR TUBE USING THE SAME

BACKGROUND OF THE INVENTION

1. Field of the Invention

The present invention relates to a non-contact type flaw detection tracking device for a pipe or tube, by which a flaw detecting sensor disposed opposite to an outer surface of a pipe or tube, for detecting a flaw on a pipe or tube such as a steel pipe or tube, accurately tracks a pipe or tube rotated in a circumferential direction during flaw detection, and an automatic flaw detecting apparatus for a pipe or tube capable of automatically detecting a flaw over the entire length of a pipe or tube including an end of the pipe or tube by using the same. Hereinafter, "pipe or tube" is referred to as "pipe" when deemed appropriate.

2. Description of the Related Art

As a nondestructive inspection method for a pipe, have been known various kinds of flaw detecting methods exemplified by an ultrasonic testing method, an eddy current testing method and a magnetic flux leakage testing method. These flaw detecting methods are generally implemented by relatively rotating a flaw detecting sensor such as an ultrasonic probe in a circumferential direction of a pipe, and further, by relatively moving the flaw detecting sensor in an axial direction of the pipe. In these flaw detecting methods, it is important to maintain positional relationship constant between the pipe relatively rotated in the circumferential direction during flaw detection and the flaw detecting sensor, that is, the positional relationship within a plane perpendicular to the axial direction of the pipe in order to keep a constant flaw detecting sensitivity.

However, it is difficult to maintain relative positional relationship between the pipe and the flaw detecting sensor constant due to the cross-sectional shape of the pipe, vibrations during transportation of the pipe or an influence by a bent pipe at, in particular, an end in the case where the position of the flaw detecting sensor, that is, the position within the plane perpendicular to the axial direction of the pipe is fixed.

In view of this, the flaw detecting sensor is attached to a contact type tracking device for bringing a mechanical contact member such as a roller or a shoe into contact with the pipe principally except for the end of the pipe in the conventional flaw detecting methods, so that a flaw is automatically detected while allowing the flaw detecting sensor to track a positional change of the pipe. In the meantime, ultrasonic testing is performed by manually scanning an ultrasonic probe or magnetic particle testing is performed at the end of the pipe, at which the contact type tracking device is hardly used for the fear of breakage of the contact member.

However, the contact member is liable to be separated from the pipe in the contact type tracking device as the rotational speed of the pipe becomes higher, and therefore, the rotational speed of the pipe must be limited due to degradation of the tracking accuracy of the flaw detecting sensor, thereby raising a problem of deterioration of a flaw detecting efficiency. In addition, the contact member need be brought into contact with the pipe, thereby raising a problem of cumbersome maintenance or a possibility of breakage of the contact member. Moreover, the manual ultrasonic testing or the magnetic particle testing at the end of the pipe requires cumbersome work and degrades the flaw detecting efficiency, and further, the magnetic particle testing, in particular, raises a problem of difficulty in quantifying the detected flaws.

In view of this, there has been desired development of a tracking device of a non-contact type, that is, without the above-described contact member, but being capable of allowing a flaw detecting sensor to track over the entire length of a pipe.

Up to now, non-contact type tracking devices have been proposed in, for example, Japanese Laid-Open Patent Publication Nos. 64-38648, 05-265559 and 2001-208730.

However, a device disclosed in Japanese Laid-Open Patent Publication No. 64-38648 is configured such that a flaw detecting sensor, that is, a probe which tracks a pipe is integrated with a non-contact type displacement gauge, that is, a displacement sensor for measuring the positional relationship between the flaw detecting sensor and the pipe, so as to control the position of the flaw detecting sensor immediately on the basis of the positional relationship between the flaw detecting sensor and the pipe measured by the displacement gauge. Therefore, there arises a problem that high tracking accuracy cannot be achieved because of an operational delay inevitably occurring in positioning means, that is, a servo mechanism disposed in the flaw detecting sensor. In other words, the high tracking accuracy requires a remarkably low rotational speed of the pipe during flaw detection, thereby raising a problem of degradation of flaw detecting efficiency.

In the meantime, a device disclosed in Japanese Laid-Open Patent Publication No. 05-265559 or 2001-208730 is configured such that a flaw detecting sensor tracks, that is, is positioned on a pipe in a stationary state, that is, during non-rotation in a circumferential direction. Therefore, it is difficult to apply such a device to the case of an ever-changing relative position between the flaw detecting sensor and the pipe due to the rotation of the pipe in the circumferential direction.

SUMMARY OF THE INVENTION

The present invention has been accomplished to solve the above-described problems in the related art. Thus, an object of the present invention is to provide a non-contact type flaw detection tracking device for a pipe or tube, by which a flaw detecting sensor disposed opposite to an outer surface of a pipe or tube, for detecting a flaw on a pipe or tube such as a steel pipe or tube, accurately tracks a pipe or tube rotated in a circumferential direction during flaw detection, and an automatic flaw detecting apparatus for a pipe or tube capable of automatically detecting a flaw over the entire length of a pipe or tube including an end of the pipe or tube by using the same.

In order to solve the above-described object, the present invention provides a flaw detecting tracking device for a pipe or tube, by which a flaw detecting sensor disposed opposite to an outer surface of a pipe or tube and relatively moving along an axial direction of the pipe or tube, for detecting a flaw on the pipe or tube rotated in a circumferential direction, tracks the pipe or tube, the tracking device comprising at least one non-contact type displacement gauge for measuring displacement at the outer surface of the pipe or tube in a non-contact state; a positioner for moving the flaw detecting sensor within a plane perpendicular to an axial direction of the pipe or tube along the opposite direction of the pipe or tube to the flaw detecting sensor and a direction perpendicular to the opposite direction; and a positioning controller for controlling the positioner, the positioning controller predicting a time until a portion of the pipe or tube whose displacement is measured by the non-contact type displacement gauge reaches a predetermined position on a straight line extending in the opposite direction through the rotational center of the pipe or tube on the basis of the positional relationship between the non-contact type displacement gauge and the flaw detecting sensor and a rotational speed of the pipe or tube; controlling the positioner on the basis of the displacement measured by the non-contact type displacement gauge and an operational delay time of the positioner in such a manner that the relative position of the flaw detecting sensor after the lapse of the predicted time to the pipe or tube after the lapse of the predicted time becomes substantially constant in the opposite direction; and moving the flaw detecting sensor along the opposite direction, and the positioning controller predicting a time until a portion of the pipe or tube whose displacement is measured by the non-contact type displacement gauge reaches a predetermined position on a straight line extending in the perpendicular direction through the rotational center of the pipe or tube on the basis of the positional relationship between the non-contact type displacement gauge and the flaw detecting sensor and a rotational speed of the pipe or tube; controlling the positioner on the basis of the displacement measured by the non-contact type displacement gauge and an operational delay time of the positioner in such a manner that the relative position of the flaw detecting sensor after the lapse of the predicted time to the pipe or tube after the lapse of the predicted time becomes substantially constant in the perpendicular direction; and moving the flaw detecting sensor along the perpendicular direction.

According to the present invention, the positioning controller controls the positioner for moving the flaw detecting sensor in such a manner that the flaw detecting sensor tracks the pipe or tube, that is, in such a manner that the positions of the flaw detecting sensor in the opposite direction and the direction perpendicular to the opposite direction become substantially constant relative to the pipe or tube, on the basis of the displacement measured by the non-contact type displacement gauge. It is unnecessary to bring a contact member such as a roller or a shoe into contact with the pipe or tube, so that the flaw detecting sensor can track the pipe or tube over the entire length of the pipe or tube even if an end of the pipe or tube is bent.

If the center of the pipe or tube is deviated from the rotational center of the pipe or tube in the state where the center of rotation of the pipe or tube in the circumferential direction (i.e., the rotational center of the pipe or tube) is constant, the center of the pipe or tube is moved on an arc about the rotational center of the pipe or tube as the pipe or tube is rotated in the circumferential direction. In the case where the pipe or tube in the direction perpendicular to the axial direction is formed into a perfect circle in cross section, the displacement of the pipe or tube from the flaw detecting sensor in the opposite direction is varied according to the displacement measured by the non-contact type displacement gauge when the portion of the pipe or tube whose displacement is measured at a position opposite to the non-contact type displacement gauge reaches the predetermined position on the straight line extending in the opposite direction, that is, in the direction of the pipe or tube opposite to the flaw detecting sensor, through the rotational center of the pipe or tube. A detailed description will be made below. For example, a distance up to the pipe or tube measured by the non-contact type displacement gauge is referred to as a reference of the displacement, that is, an origin of the non-contact type displacement gauge in the case where the pipe or tube in the direction perpendicular to the axial direction is formed into a perfect circle in cross section, and further, where the center of the pipe or tube is coincident with the rotational center of the pipe or tube. In the same manner, a distance between the flaw detecting sensor facing the center of the pipe or tube and the pipe or tube in the opposite direction is set as a reference of the displacement in the opposite direction, that is, an origin of the flaw detecting sensor in the opposite direction in the case where the pipe or tube is formed into a perfect circle in cross section in the direction perpendicular to the axial direction, and further, where the center of the pipe or tube is coincident with the rotational center of the pipe or tube. At this time, an absolute value of the displacement measured by the non-contact type displacement gauge, that is, the distance from the origin of the non-contact type displacement gauge in the case where the center of the pipe or tube is deviated from the rotational center of the pipe or tube is equal to an absolute value of the displacement of the pipe or tube from the flaw detecting sensor in the opposite direction, that is, the distance from the origin of the flaw detecting sensor in the opposite direction in the case where the center of the pipe or tube is deviated from the rotational center of the pipe or tube. As a consequence, according to the present invention, the time until the portion of the pipe or tube whose displacement is measured by the non-contact type displacement gauge reaches the predetermined position on the straight line extending in the opposite direction through the rotational center of the pipe or tube is predicted on the basis of the positional relationship between the non-contact type displacement gauge and the flaw detecting sensor and the rotational speed of the pipe or tube; and the flaw detecting sensor is moved along the opposite direction on the basis of the displacement measured by the non-contact type displacement gauge (as described above, the absolute value of the displacement becomes equal to the absolute value of the displacement of the pipe or tube in the opposite direction from the flaw detecting sensor after the lapse of the predicted time) in such a manner that the relative position of the flaw detecting sensor after the lapse of the predicted time to the pipe or tube after the lapse of the predicted time becomes substantially constant in the opposite direction. Thus, the flaw detecting sensor can accurately track the pipe or tube.

In the same manner, the position of the flaw detecting sensor facing the center of the pipe or tube is referred to as a reference of the displacement in the perpendicular direction, that is, an origin of the flaw detecting sensor in the perpendicular direction in the case where the pipe or tube is formed into a shape of a perfect circle in cross section in the direction perpendicular to the axial direction of the pipe or tube, and further, where the center of the pipe or tube is coincident with the rotational center of the pipe or tube. At this time, when the portion of the pipe or tube whose displacement is measured at a position opposite to the non-contact type displacement gauge reaches the predetermined position on the straight line extending in the perpendicular direction through the rotational center of the pipe or tube, the absolute value of the displacement measured by the non-contact type displacement gauge, that is, the distance from the origin of the non-contact type displacement gauge in the case where the center of the pipe or tube is deviated from the rotational center of the pipe or tube is equal to the absolute value of the displacement of the center of the pipe or tube in the perpendicular direction from the flaw detecting sensor, that is, the distance from the origin of the flaw detecting sensor in the perpendicular direction in the case where the center of the pipe or tube is deviated from the rotational center of the pipe or tube. As a consequence, according to the present invention, the time until the portion of the pipe or tube whose displacement is measured by the non-contact type displacement gauge reaches the predetermined position on the straight line extending in the perpendicular direction through the rotational center of the pipe or tube is predicted on the basis of the positional relationship between the non-contact type displacement gauge and the flaw detecting sensor and the rotational speed of the pipe or tube; and the flaw detecting sensor is moved along the perpendicular direction on the basis of the displacement measured by the non-contact type displacement gauge (as described above, the absolute value of the displacement becomes equal to the absolute value of the displacement of the center of the pipe or tube in the perpendicular direction from the flaw detecting sensor after the lapse of the predicted time) in such a manner that the relative position of the flaw detecting sensor after the lapse of the predicted time to the pipe or tube after the lapse of the predicted time becomes substantially constant in the perpendicular direction. Thus, the flaw detecting sensor can accurately track the pipe or tube.

Furthermore, according to the present invention, the non-contact type displacement gauge and the flaw detecting sensor are disposed at positions different from each other along the circumferential direction of the pipe or tube, so that it is unnecessary to control the positioner immediately, that is, to control the position of the flaw detecting sensor on the basis of the displacement measured by the non-contact type displacement gauge in simultaneous consideration of the operational delay time of the positioner such as mechanical or electric delay time from issuance of an operation starting command to the positioner to actual operation start. Thus, it is possible to achieve the high tracking accuracy.

Preferably, the flaw detecting tracking device for a pipe or tube further comprises at least two non-contact type displacement gauges disposed along the opposite direction and the perpendicular direction, respectively, wherein the positioning controller predicts a time until a portion of the pipe or tube whose displacement is measured by the non-contact type displacement gauge disposed along the opposite direction reaches a predetermined position on a straight line extending in the opposite direction through the rotational center of the pipe or tube on the basis of the positional relationship between the non-contact type displacement gauge disposed along the opposite direction and the flaw detecting sensor and a rotational speed of the pipe or tube, controls the positioner on the basis of the displacement measured by the non-contact type displacement gauge disposed along the opposite direction and an operational delay time of the positioner in such a manner that the relative position of the flaw detecting sensor after the lapse of the predicted time to the pipe or tube after the lapse of the predicted time becomes substantially constant in the opposite direction, and moves the flaw detecting sensor along the opposite direction, and the positioning controller predicts a time until a portion of the pipe or tube whose displacement is measured by the non-contact type displacement gauge disposed along the perpendicular direction reaches a predetermined position on a straight line extending in the perpendicular direction through the rotational center of the pipe or tube on the basis of the positional relationship between the non-contact type displacement gauge disposed along the perpendicular direction and the flaw detecting sensor and a rotational speed of the pipe or tube, controls the positioner on the basis of the displacement measured by the non-contact type displacement gauge disposed along the perpendicular direction and an operational delay time of the positioner in such a manner that the relative position of the flaw detecting sensor after the lapse of the predicted time to the pipe or tube after the lapse of the predicted time becomes substantially constant in the perpendicular direction, and moves the flaw detecting sensor along the perpendicular direction.

With the above-described preferred configuration, the flaw detecting sensor is moved along the opposite direction on the basis of the displacement measured by the non-contact type displacement gauge disposed along the opposite direction. In the meantime, the flaw detecting sensor is moved along the perpendicular direction on the basis of the displacement measured by the non-contact type displacement gauge disposed along the perpendicular direction. In other words, the displacement measurement direction coincides with the movement direction of the flaw detecting sensor on the basis of the measured displacement, so that the flaw detecting sensor is expected to even more accurately track the pipe or tube.

For example, in the case where the portion of the pipe or tube whose displacement is measured at the position opposite to the non-contact type displacement gauge disposed along the perpendicular direction is a long- or short-diameter portion of an ellipse when the pipe or tube is formed into the shape of an ellipse in cross section in the direction perpendicular to the axial direction, displacement similar to the displacement when the center of the pipe or tube is deviated from the rotational center of the pipe or tube (when the pipe or tube is formed into the shape of a perfect circle and the center of the pipe or tube is deviated from the rotational center of the pipe or tube) is measured even if the center of the pipe or tube is not deviated from the rotational center of the pipe or tube. Specifically, if the portion of the pipe or tube whose displacement is measured is a long-diameter portion of the ellipse, displacement becomes smaller than the origin of the non-contact type displacement gauge, that is, negative displacement. In contrast, if the portion is a short-diameter portion, displacement becomes greater than the origin of the non-contact type displacement gauge, that is, positive displacement. As a consequence, when the flaw detecting sensor is moved along the perpendicular direction on the basis of the measured displacement, the flaw detecting sensor is moved even though the center of the pipe or tube is not deviated from the rotational center of the pipe or tube (so that the flaw detecting sensor need not be moved along the perpendicular direction), whereby the tracking accuracy is possibly degraded.

In order to prevent the tracking accuracy from being degraded, the flaw detecting tracking device for a pipe or tube further comprises a pair of non-contact type displacement gauges disposed opposite to each other in the perpendicular direction with a pipe or tube interposed therebetween, wherein the positioning controller predicts a time until a portion of the pipe or tube whose displacement is measured by the pair of non-contact type displacement gauges reaches a predetermined position on a straight line extending in the perpendicular direction through the rotational center of the pipe or tube on the basis of the positional relationship between the pair of non-contact type displacement gauges and the flaw detecting sensor and a rotational speed of the pipe or tube, controls the positioner on the basis of a difference between displacement measured by one of the non-contact type displacement gauges and displacement measured by the other non-contact type displacement gauge and an operational delay time of the positioner in such a manner that the relative position of the flaw detecting sensor after the lapse of the predicted time to the pipe or tube after the lapse of the predicted time becomes substantially constant in the perpendicular direction, and moves the flaw detecting sensor along the perpendicular direction, and the positioning controller predicts a time until a portion of the pipe or tube whose displacement is measured by any one selected from among the pair of non-contact type displacement gauges and the other non-contact type displacement gauge reaches a predetermined position on a straight line extending in the opposite direction through the rotational center of the pipe or tube on the basis of the positional relationship between the selected non-contact type displacement gauge and the flaw detecting sensor and a rotational speed of the pipe or tube, controls the positioner on the basis of displacement measured by the selected non-contact type displacement gauge and an operational delay time of the positioner in such a manner that the relative position of the flaw detecting sensor after the lapse of the predicted time to the pipe or tube after the lapse of the predicted time becomes substantially constant in the opposite direction, and moves the flaw detecting sensor along the opposite direction.

In the above-described preferred configuration, the flaw detecting sensor is moved along the perpendicular direction on the basis of the difference between the displacement measured by one non-contact type displacement gauge out of the pair of non-contact type displacement gauges disposed opposite to each other along the perpendicular direction with the pipe or tube interposed therebetween and the displacement measured by the other non-contact type displacement gauge. Consequently, the difference between the displacement amounts measured by both of the non-contact type displacement gauges becomes zero in the case where the center of the pipe or tube is coincident with the rotational center of the pipe or tube even if the pipe or tube is formed into the shape of an ellipse in cross section, so that the flaw detecting sensor need not be moved along the perpendicular direction, thus maintaining the tracking accuracy.

Preferably, the positioning controller calculates an outer diameter of the pipe or tube on the basis of the displacements measured by the pair of non-contact type displacement gauges.

In the above-described preferred configuration, the pair of non-contact type displacement gauges provided in the tracking device can be used in not only allowing the flaw detecting sensor to track the pipe or tube but also calculating the outer diameter of the pipe or tube, with an attendant convenience in no need of independent provision of an outer diameter measuring device. Here, the distance from each of the non-contact type displacement gauges to the outer surface of the pipe or tube is calculated on the basis of the displacement measured by each of the non-contact type displacement gauges, or the distance up to the outer surface of the pipe or tube is directly measured by each of the non-contact type displacement gauges, and then, the calculated distance from each of the non-contact type displacement gauges to the outer surface of the pipe or tube is subtracted from a separation distance from each of the non-contact type displacement gauges, thus determining the outer diameter of the pipe or tube.

As the non-contact type displacement gauge, it is possible to use, for example, an eddy current type displacement gauge which utilizes a change in eddy current produced in an object whose displacement is to be measured according to the distance up to the object whose displacement is to be measured. Here, since the magnitude of eddy current is varied according to the material (specifically, such as magnetic permeability or conductivity) of the pipe or tube as the object whose displacement is to be measured according to the present invention, it is preferable that the measured displacement should be corrected according to the material of the pipe or tube.

Therefore, it is preferable that the non-contact type displacement gauge is an eddy current type displacement gauge, and the positioning controller corrects the displacement measured by the non-contact type displacement gauge according to a material of the pipe or tube, to control the positioner on the basis of the corrected displacement.

As the flaw detecting sensor, it is possible to use, for example, an ultrasonic probe. In order to enhance the flaw detecting sensitivity of the ultrasonic probe, it is preferable that the initial position of the ultrasonic probe in the perpendicular direction should be set at a position where an echo intensity received from the outer surface of the pipe or tube by the ultrasonic probe becomes highest.

Therefore, it is preferable that the flaw detecting sensor is an ultrasonic probe, and the positioning controller controls the positioner with respect to the pipe or tube in a stationary state, moves the ultrasonic probe along the perpendicular direction, and sets, as an initial position of the ultrasonic probe, a position at which an echo intensity received from the outer surface of the pipe or tube by the ultrasonic probe becomes highest.

Here, in order to solve the above-described object, the present invention further provides an automatic flaw detecting apparatus for a pipe or tube comprising any one of the flaw detection tracking devices for the pipe or tube; and a flaw detecting sensor for tracking the pipe or tube by the flaw detection tracking device for the pipe or tube.

According to the present invention, there are provided the non-contact type flaw detection tracking device for a pipe or tube, by which the flaw detecting sensor disposed opposite to the outer surface of the pipe or tube, for detecting a flaw on the pipe or tube such as a steel pipe or tube, accurately tracks the pipe or tube rotated in the circumferential direction during flaw detection, and the automatic flaw detecting apparatus for a pipe or tube capable of automatically detecting a flaw over the entire length of the pipe or tube including the end of the pipe or tube by using the same.

DETAILED DESCRIPTION OF THE PREFERRED EMBODIMENTS

A description will be given below on preferred embodiments according to the present invention appropriately with reference to the attached drawings.

First Embodiment

Figure 1A:
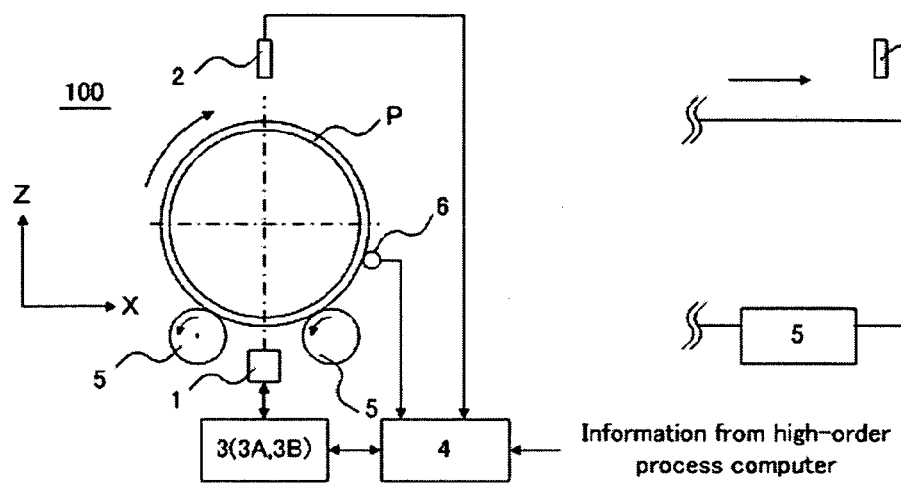
FIGS. 1A and 1B are diagrams schematically illustrating the configuration of a flaw detection tracking device for a pipe in a first embodiment according to the present invention.
Figure 1B:
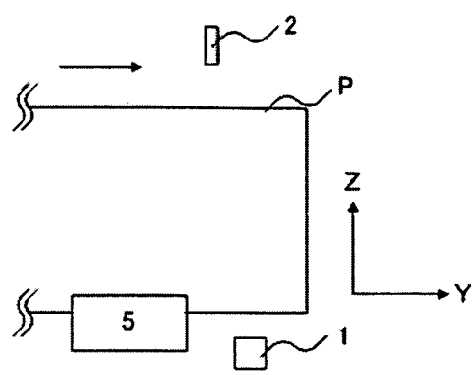

FIGS. 1A and 1B are diagrams schematically illustrating the configuration of a flaw detection tracking device for a pipe in a first embodiment according to the present invention, wherein FIG. 1A is a front view, as viewed in an axial direction of a pipe and FIG. 1B is a side view, as viewed in a direction perpendicular to the axial direction of the pipe. As illustrated in FIGS. 1A and 1B, a flaw detection tracking device for a pipe (hereinafter, appropriately simply referred to as "a tracking device") 100 in the present embodiment is a device adapted to allow a flaw detecting sensor 1, which is disposed opposite to the outer surface of a pipe P and is relatively moved in the axial direction of the pipe P, (the pipe P is moved in the axial direction in the present embodiment), to track the pipe P, so as to detect a flaw on the pipe P rotated in a circumferential direction.

In the present embodiment, the flaw detecting sensor 1 and the tracking device 100, specifically, a non-contact type displacement gauge 2, which will be described later, constituting the tracking device 100, are not moved but fixed in the axial direction of the pipe P. Furthermore, the pipe P is supported by turning rollers 5 whose rotation allows the pipe to be rotated in the circumferential direction and be conveyed in the axial direction. The flaw detecting sensor 1 is disposed downstream in a conveyance direction of the pipe P, that is, downstream beyond the turning roller 5 arranged most downstream, and under the pipe P in a vertical direction. However, the present invention is not limited to this. For example, the present invention may be configured such that the pipe P is not conveyed in the axial direction but is only rotated in the circumferential direction, and further, that the flaw detecting sensor 1 and the tracking device 100, that is, the non-contact type displacement gauge 2, are moved in the axial direction of the pipe P. Moreover, the disposing position of the flaw detecting sensor 1 is not limited to the position under the pipe P in the vertical direction. For example, the flaw detecting sensor 1 may be disposed at any position along the circumferential direction of the pipe P as long as a fixing space or the like is not restricted.

The tracking device 100 includes at least one non-contact type displacement gauge 2, which is disposed opposite to the outer surface of the pipe P so as to measure displacement at the outer surface of the pipe P without any contact; a positioner 3 which moves the flaw detecting sensor 1 within a plane perpendicular to the axial direction of the pipe P along the opposite direction of the pipe P to the flaw detecting sensor 1 and a direction perpendicular to the opposite direction; and a positioning controller 4 which controls the positioner 3.

In the present embodiment, one non-contact type displacement gauge 2 is disposed downstream in the conveyance direction of the pipe P, that is, downstream beyond the turning roller 5 arranged most downstream, and above the pipe P in the vertical direction. However, the present invention is not limited to this. For example, the flaw detecting sensor 1 may be disposed at any position along the circumferential direction of the pipe P as long as the non-contact type displacement gauge 2 is disposed at a position different from the flaw detecting sensor 1 and the fixing space or the like is not restricted. Here, the non-contact type displacement gauge 2 in the present embodiment is preferably an eddy current type displacement gauge which utilizes a change in eddy current produced in an object whose displacement is to be measured according to a distance up to the object whose displacement is to be measured.

The positioner 3 in the present embodiment is configured in such a manner as to move the flaw detecting sensor 1 within a plane perpendicular to the axial direction of the pipe P in the vertical direction (i.e., a Z-axis direction) and in a horizontal direction (i.e., an X-axis direction) perpendicular to the axial direction of the pipe P. In the present embodiment, the positioner 3 includes a positioner 3A, which moves the flaw detecting sensor 1 along the Z-axis direction, and another positioner 3B, which moves the flaw detecting sensor 1 along the X-axis direction. Here, the positioner 3A and the positioner 3B can adopt the same constitution except for the difference in direction of reciprocating motion of a piston rod 311, which will be described later.

Figure 2:
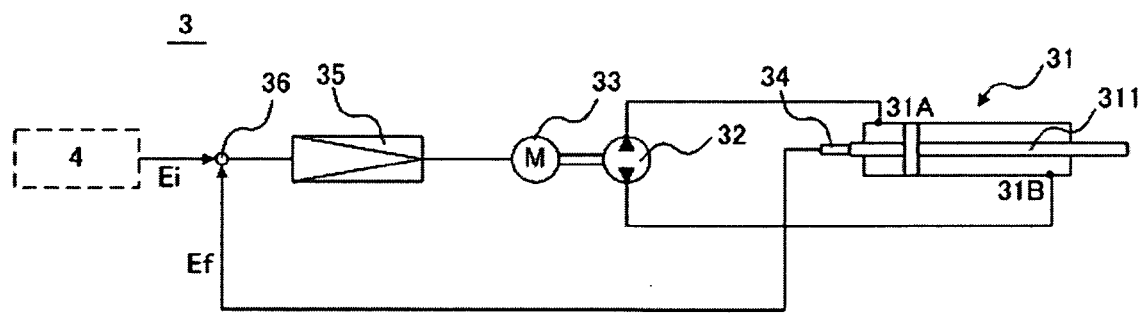
FIG. 2 is a diagram schematically illustrating the configuration of a positioner illustrated in FIG. 1.

FIG. 2 is a diagram schematically illustrating the configuration of the positioner 3 (3A or 3B) in the present embodiment. As illustrated in FIG. 2, the positioner 3 in the present embodiment is provided with a hydraulic cylinder 31, a hydraulic pump 32, a servomotor 33, a linear scale 34, a servo amplifier 35 and an adder 36. The hydraulic pump 32 is a bidirectional pump which is rotationally driven forward and backward by the servomotor 33. Pressure oil is switchably supplied to or discharged from a port 31A on a forward side and a port 31B on a backward side in the hydraulic cylinder 31 by switching the rotational direction of the hydraulic pump 32. When the pressure oil is supplied to the port 31A while being discharged from the port 31B, the piston rod 311 in the hydraulic cylinder 31 is moved forward (in other words, is moved rightward on the sheet of FIG. 2). In contrast, when the pressure oil is discharged from the port 31A while being supplied to the port 31B, the piston rod 311 is moved backward (in other words, is moved leftward on the sheet of FIG. 2). The flaw detecting sensor 1 is fixed to the piston rod 311 in the hydraulic cylinder 31, and thus, is moved along the Z-axis direction (in the case of the positioner 3A) or the X-axis direction (in the case of the positioner 3B) according to the reciprocating motion of the piston rod 311.

The linear scale 34 is configured in such a manner as to detect actual displacement of the piston rod 311. An output voltage Ef from the linear scale 34 corresponding to the displacement of the piston rod 311 is fed back to the adder 36, which compares the output voltage Ef with an input voltage Ei from the positioning controller 4 (corresponding to the movement amount of the flaw detecting sensor 1 along the Z-axis direction or the X-axis direction, so as to track the pipe P). Thereafter, a difference between the input voltage Ei and the output voltage Ef is amplified by the servo amplifier 35, thus to be supplied for driving the servomotor 33.

As described above, the positioner 3 in the present embodiment is configured to perform a so-called servo control with high positioning accuracy. It is unnecessary to provide an oil tank, various pipelines, a control valve and the like in addition to abrasion parts such as a ball screw or a linear bearing, which are needed in a general hydraulic actuator, thus reducing the size and producing an advantage of facilitation of maintenance.

The positioning controller 4 in the present embodiment is a general-purpose computer or an appropriate electronic circuit connected thereto. The positioning controller 4 receives information on the positional relationship between the non-contact type displacement gauge 2 and the flaw detecting sensor 1 (the positional relationship in the present embodiment, in which the non-contact type displacement gauge 2 and the flaw detecting sensor 1 are arranged in separation from each other at an angle of 180 degrees in the circumferential direction of the pipe P), the rotational speed of the pipe P, the outer diameter or material of the pipe P, an operational delay time of the positioner 3 and the like. The positioning controller 4 may receive the information through manual direct input or from a high-order process computer. As to the rotational speed of the pipe P, in particular, the tracking accuracy of the flaw detecting sensor 1 is expected to be enhanced by the use of an actual value, not a set value. In view of this, there may be adopted a configuration in which a pulse generator (abbreviated as "a PLG") 6, for example, is disposed in contact with the outer surface of the pipe P, and the positioning controller 4 calculates the rotational speed of the pipe P on the basis of a value outputted from the PLG 6 and a ratio of the outer diameter of the PLG 6 to the outer diameter of the pipe P. Alternatively, there may be adopted another configuration in which a pulse generator (abbreviated as "a PLG") 6 for detecting the rotational speed of the turning roller 5 is attached to the turning roller 5, and the positioning controller 4 calculates the rotational speed of the pipe P on the basis of a value outputted from the PLG 6 and a ratio of the outer diameter of the turning roller 5 to the outer diameter of the pipe P. Alternatively, there may be adopted another configuration in which a speedometer (not shown) for measuring a circumferential speed at the outer surface of the pipe P is attached, and the positioning controller 4 calculates the rotational speed of the pipe P on the basis of a value outputted from the speedometer and the outer diameter of the pipe P.

Hereinafter, descriptions will be given on initial setting and operation of the tracking device 100 configured as described above.

(1) Setting Correction Coefficient with Respect to Value Measured by Non-Contact Type Displacement Gauge As described above, although the eddy current type displacement gauge is used as the non-contact type displacement gauge 2 in the present embodiment, it is preferable that displacement measured by the non-contact type displacement gauge 2 should be corrected according to the material of the pipe P since the magnitude of the eddy current also variably depends upon the material of the pipe P (magnetic permeability or conductivity). As a consequence, the positioning controller 4 previously stores therein correction coefficients with respect to the displacement measured by the non-contact type displacement gauge 2 according to materials of the pipe P in the form of, for example, a table. As described above, the positioning controller 4 stores therein data on the material of the pipe P. Consequently, the positioning controller 4 selects a correction coefficient according to the input data on the material of the pipe P from the table, corrects to multiply the displacement, which is measured by the non-contact type displacement gauge 2, by the selected correction coefficient, and thus, controls the positioner 3 on the basis of the corrected displacement.

(2) Setting Position of Non-Contact Type Displacement Gauge

A position of the non-contact type displacement gauge 2 in the X-axis direction can be fixedly set at, for example, an intermediate point between the pair of turning rollers 5 juxtaposed in the X-axis direction. Alternatively, the non-contact type displacement gauge 2 may be fixed to, for example, an appropriate moving stage capable of moving the non-contact type displacement gauge 2 in the X-axis direction, so that the non-contact type displacement gauge 2 is moved in the X-axis direction in a state where the pipe P is disposed thereunder in a stationary manner, wherein it is preferable that the pipe P should be formed into substantially a perfect circle in cross section in the direction perpendicular to the axial direction and almost without bend, thus positioning the non-contact type displacement gauge 2 at a position nearest the pipe P to be measured by the non-contact type displacement gauge 2, wherein that position corresponds to a position facing the center of the pipe P.

A proper position of the non-contact type displacement gauge 2 in the Z-axis direction is varied according to the outer diameter of the pipe P whose flaw is to be detected. Therefore, the non-contact type displacement gauge 2 may be fixed to, for example, an appropriate moving stage capable of moving the non-contact type displacement gauge 2 in the Z-axis direction, so that the non-contact type displacement gauge 2 is moved in the Z-axis direction in a state where the pipe P is disposed thereunder in a stationary manner, wherein it is preferable that the pipe P should be formed into substantially a perfect circle in cross section in the direction perpendicular to the axial direction and almost without bend, thus positioning the non-contact type displacement gauge 2 at a position where a distance up to the pipe P to be measured by the non-contact type displacement gauge 2 may be set at, for example, substantially a middle position within a distance measurement range of the non-contact type displacement gauge 2. The distance up to the pipe P to be measured by the non-contact type displacement gauge 2 positionally set as described above is referred to as a reference (origin) of displacement, and thus, a distance from the origin is outputted as displacement.

(3) Setting Initial Position of Flaw Detecting Sensor

An initial position of the flaw detecting sensor 1 in the X-axis direction may be fixedly set at, for example, an intermediate point between the pair of turning rollers 5 juxtaposed in the X-axis direction. However, a position at which an actual flaw detecting sensitivity becomes highest is detected, and then, that position is preferably set as the initial position in the X-axis direction. In view of this, in the case where an ultrasonic probe, for example, is used as the flaw detecting sensor 1, the positioner 3 is controlled to move the ultrasonic probe in the X-axis direction in a state where the pipe P is disposed thereabove in a stationary manner, wherein it is preferable that the pipe P should be formed into substantially a perfect circle in cross section in the direction perpendicular to the axial direction and almost without bend, so that a position at which an echo intensity from the outer surface of the pipe P received by the ultrasonic probe becomes highest may be set as the initial position of the ultrasonic probe.

A separation distance between the flaw detecting sensor 1 and the pipe P is not so varied even with a change in outer diameter of the pipe P since the flaw detecting sensor 1 is disposed under the pipe P supported by the turning rollers 5 in the vertical direction in the present embodiment. Moreover, in the case where the ultrasonic probe is used as the flaw detecting sensor 1, the flaw detecting sensitivity is seldom influenced even by a slight fluctuation in the separation distance from the pipe P. As a consequence, the initial position of the flaw detecting sensor 1 in the Z-axis direction can be fixedly set at a position where a predetermined flaw detecting sensitivity can be achieved. Here, in the case where the flaw detecting sensor 1 is disposed above the pipe P in the vertical direction, the separation distance between the flaw detecting sensor 1 and the pipe P is varied according to the outer diameter of the pipe P when the position of the flaw detecting sensor 1 is fixed. In this case, it is preferable that a position at which a constant separation distance can be kept should be set as the initial position by moving the flaw detecting sensor 1 in the Z-axis direction according to the outer diameter of the pipe P.

(4) Operation of Positioning Controller 4

After the initial setting described in the above items (1) to (3), the pipe P as a member whose flaw is to be actually detected is conveyed in the axial direction while being rotated in the circumferential direction by the turning rollers 5. At this time, the positioning controller 4 actuates in the manner described below, to allow the flaw detecting sensor 1 to track the pipe P.

First of all, the positioning controller 4 predicts a time until a portion of the pipe P whose displacement is measured by the non-contact type displacement gauge 2 reaches a predetermined position, for example, a position after rotation by 180° on a straight line extending in the Z-axis direction through the rotational center of the pipe P on the basis of the inputted positional relationship between the non-contact type displacement gauge 2 and the flaw detecting sensor 1, that is, the positional relationship between the non-contact type displacement gauge 2 and the flaw detecting sensor 1 which are disposed in separation from each other at 180° in the circumferential direction of the pipe P, and the inputted rotational speed of the pipe. For example, a time Taz until the portion of the pipe P whose displacement is measured by the non-contact type displacement gauge 2 reaches the position after the rotation by 180° is predicted from the following expression: Taz=1/2N (min), wherein N (rpm) designates the rotational speed of the pipe P.

Next, the positioning controller 4 controls the positioner 3A on the basis of the displacement measured by the non-contact type displacement gauge 2 and an inputted operational delay time of the positioner 3A in such a manner that the flaw detecting sensor 1 in the Z-axis direction after the lapse of the predicted time Taz is substantially constantly positioned relative to the pipe P after the lapse of the predicted time Taz, and then, moves the flaw detecting sensor 1 in the Z-axis direction. For example, when the operational delay time of the positioner 3A is assumed to be a time Tba, the positioning controller 4 instructs the positioner 3A to start moving the flaw detecting sensor 1 from the initial position by a predetermined movement amount in the Z-axis direction after the lapse of a time Taz to Tba after the measurement of the displacement by the non-contact type displacement gauge 2, that is, outputs the voltage Ei (see FIG. 2) corresponding to the movement amount.

On the assumption that, for example, the displacement measured by the non-contact type displacement gauge 2 is denoted by—$\alpha$, which signifies the approach of the outer surface of the pipe P toward the non-contact type displacement gauge 2 from the origin by the amount $\alpha$, the movement amount of the flaw detecting sensor 1 in the Z-axis direction is expressed by $\alpha$ in the direction of separation from the pipe P, or a value obtained by multiplying the amount $\alpha$ by a relaxation coefficient k, in which $0 \leq k \leq 1$. This reason will be explained below with reference to FIG. 3.

Figure 3:
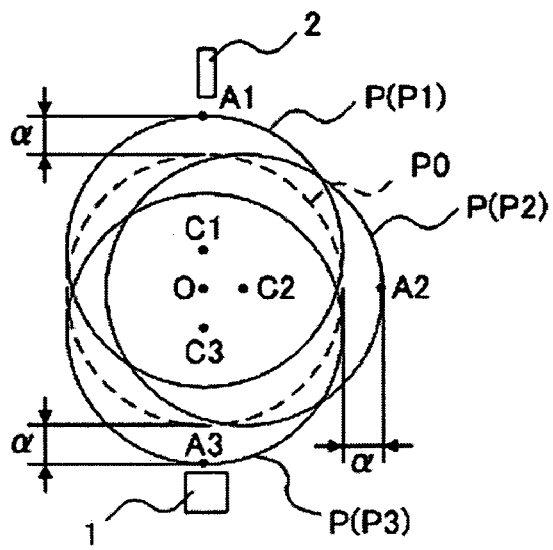
FIG. 3 is a diagram illustrating the principle of the tracking device shown in FIG. 1.

FIG. 3 is a diagram illustrating the principle of the tracking device in the present embodiment. As illustrated in FIG. 3, assume that a pipe P0 for use in setting the above-described position of the non-contact type displacement gauge 2 is formed into a perfect circle in cross section in the direction perpendicular to the axial direction, that the center of the pipe P0 is coincident with a rotational center O of the pipe P0, and that the distance up to the pipe P0 measured by the non-contact type displacement gauge 2 is referred to as the reference of the displacement, that is, the origin of the non-contact type displacement gauge 2. In the same manner, assume that the pipe P0 is used also in setting the above-described initial position of the flaw detecting sensor 1, that the initial position of the flaw detecting sensor 1 faces the center O of the pipe P0, and that a distance between the flaw detecting sensor 1 and the pipe P0 in the Z-axis direction is referred to as the reference of the displacement in the Z-axis direction, that is, the origin of the flaw detecting sensor 1 in the Z-axis direction.

After the above-described initial setting, assume that the pipe P as a member whose flaw is to be actually detected, which has an outer diameter equal to that of the pipe P0 and is formed into a perfect circle in cross section, is conveyed to a position under the non-contact type displacement gauge 2, wherein the pipe P immediately after being conveyed is referred to as a pipe P1. If the center of the pipe P is deviated from the rotational center O of the pipe P by a deviation amount $\alpha$ due to a bend in the pipe P, the center of the pipe P is moved along an arc having a radius $\alpha$ about the rotational center O of the pipe according to the rotation of the pipe P in the circumferential direction. Specifically, as illustrated in FIG. 3, a center C1 of the pipe P1 immediately after the conveyance, a center C2 of a pipe P2 after the rotation by 90° and a center C3 of a pipe P3 after the rotation by 180° are all located on the arc around the rotational center O of the pipe P. When a portion A1 of the pipe P1 whose displacement—$\alpha$ is measured at a position facing the non-contact type displacement gauge 2 reaches a portion A3 of the pipe P3 after the rotation by 180°, displacement of the pipe P3 in the Z-axis direction from the flaw detecting sensor 1 also becomes—$\alpha$, that is, the pipe P approaches the flaw detecting sensor 1 by $\alpha$. As a consequence, the movement amount of the flaw detecting sensor 1 in the Z-axis direction when the pipe P1 reaches the portion A3 of the pipe P3 after the rotation by 180° is set to $\alpha$ in the direction of separation from the pipe P3, so that the relative position of the flaw detecting sensor 1 in the Z-axis direction to the pipe P3 can be substantially constant, that is, substantially the same as the position of the flaw detecting sensor 1 in the Z-axis direction relative to the pipe P0 at the initial position.

The above-described principle presumes that the cross-sectional shape of the pipe P0 or the pipe P is a perfect circle and the rotational center O of the pipe P is invariably constant. Therefore, the operation is hardly performed in actuality in accordance with the above-described principle. If the displacement $\alpha$ per se is regarded as the movement amount of the flaw detecting sensor 1, there may occur a problem of degradation of the tracking accuracy. In order to avoid such a problem, it is preferable that the value obtained by multiplying the displacement $\alpha$ by the predetermined relaxation coefficient k, wherein $0<k<1$, should be set as the movement amount of the flaw detecting sensor 1.

In the meantime, simultaneously with the calculation of the above-described predicted time Taz, the positioning controller 4 predicts a time until a portion of the pipe P whose displacement is measured by the non-contact type displacement gauge 2 reaches a predetermined position, for example, a position after rotation by 90° on a straight line extending in the X-axis direction through the rotational center of the pipe P on the basis of the inputted positional relationship between the non-contact type displacement gauge 2 and the flaw detecting sensor 1 and the inputted rotational speed of the pipe. For example, a time Tax until the portion of the pipe P whose displacement is measured by the non-contact type displacement gauge 2 reaches the position after the rotation by 90° is predicted from the following expression: Tax=1/4N (min), wherein N (rpm) designates the rotational speed of the pipe P.

Next, the positioning controller 4 controls the positioner 3B on the basis of the displacement measured by the non-contact type displacement gauge 2 and an inputted operational delay time of the positioner 3B in such a manner that the flaw detecting sensor 1 in the X-axis direction after the lapse of the predicted time Tax is substantially constantly positioned relative to the pipe P after the lapse of the predicted time Tax, and then, moves the flaw detecting sensor 1 in the X-axis direction. For example, when the operational delay time of the positioner 3B is assumed to be a time Tbb, the positioning controller 4 instructs the positioner 3B to start moving the flaw detecting sensor 1 from the initial position by a predetermined movement amount in the X-axis direction after the lapse of a time Tax to Tbb after the measurement of the displacement by the non-contact type displacement gauge 2, that is, outputs the voltage Ei (see FIG. 2) corresponding to the movement amount.

In the same manner as described above, as illustrated in FIG. 3, assume that the displacement measured by the non-contact type displacement gauge 2 is denoted by—α, the movement amount of the flaw detecting sensor 1 in the X-axis direction is expressed by α rightward on the sheet in FIG. 3, or the value obtained by multiplying the amount α by the relaxation coefficient k, in which 0<k<1. When the portion A1 of the pipe P1 whose displacement—α is measured at a position facing the non-contact type displacement gauge 2 reaches the portion A2 of the pipe P2 after the rotation by 90°, displacement of the center C2 of the pipe P2 in the X-axis direction from the flaw detecting sensor 1 becomes—α, that is, the pipe P is moved by α rightward on the sheet in FIG. 3. As a consequence, the movement amount of the flaw detecting sensor 1 in the X-axis direction when the pipe P1 reaches the portion A2 of the pipe P2 after the rotation by 90° is set to α rightward on the sheet in FIG. 3, so that the position of the flaw detecting sensor 1 in the X-axis direction relative to the pipe P2 can be substantially constant, that is, substantially the same as the position of the flaw detecting sensor 1 in the X-axis direction relative to the pipe P0 at the initial position. In order to avoid the problem of degradation of the tracking accuracy, it is preferable that the value obtained by multiplying the displacement α by the predetermined relaxation coefficient k, wherein 0<k<1, should be set as the movement amount of the flaw detecting sensor 1 in the same manner as described above.

The above-described tracking device 100 in the present embodiment can allow the flaw detecting sensor 1 disposed opposite to the outer surface of the pipe P, for detecting a flaw on the pipe P to accurately track the pipe P rotated in the circumferential direction during the flaw detection, and further, can automatically detect a flaw over the entire length of the pipe P including the end of the pipe.

Second Embodiment

Figure 4:
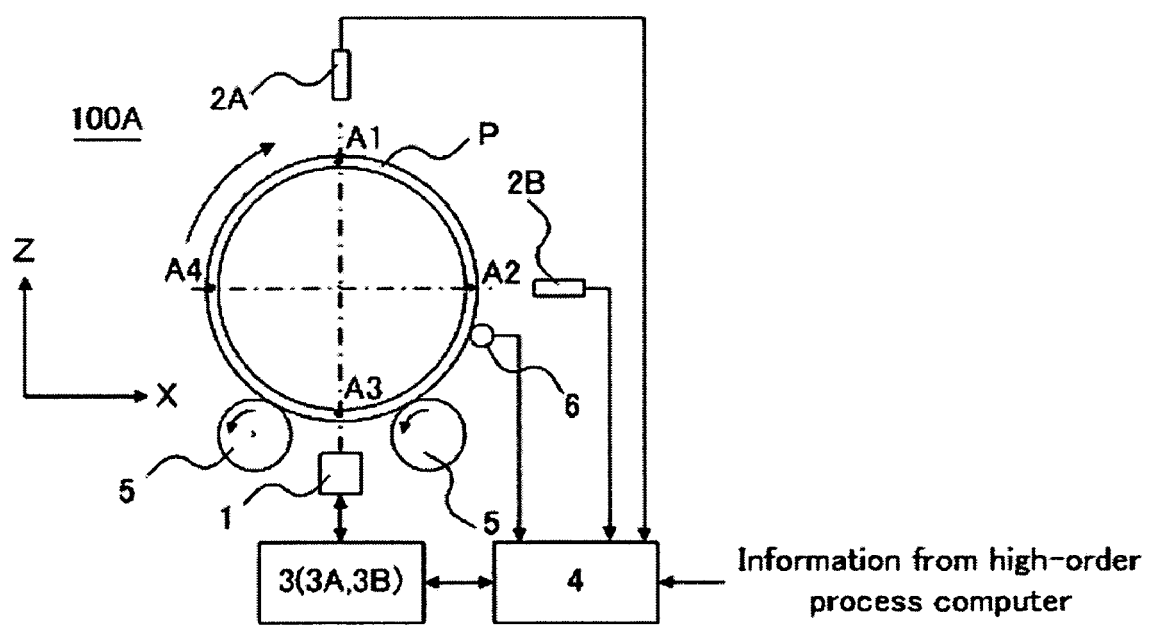
FIG. 4 is a front view schematically showing the configuration of a flaw detection tracking device for a pipe in a second embodiment according to the present invention.

FIG. 4 is a front view schematically showing the configuration of a flaw detection tracking device for a pipe in a second embodiment according to the present invention. As illustrated in FIG. 4, a tracking device 100A in the present embodiment is a device adapted to allow a flaw detecting sensor 1, which is disposed opposite to the outer surface of a pipe P and is relatively moved in the axial direction of the pipe P, to track the pipe P, so as to detect a flaw on the pipe P rotated in a circumferential direction, like in the first embodiment. Hereinafter, a description will be given on only points different from the first embodiment, and therefore, description on the same points will be omitted.

The tracking device 100A in the present embodiment includes at least two non-contact type displacement gauges 2A and 2B (two in the present embodiment) arranged in Z- and X-axis directions, respectively. The non-contact type displacement gauge 2B may be fixed to, for example, an appropriate moving stage capable of moving the non-contact type displacement gauge 2B in the Z-axis direction, so that the non-contact type displacement gauge 2B is moved in the Z-axis direction in a state where the pipe P is mounted on turning rollers 5 in a stationary manner, wherein it is preferable that the pipe P should be formed into substantially a perfect circle in cross section in a direction perpendicular to the axial direction and almost without bend, thus positioning the non-contact type displacement gauge 2B at a position nearest to the pipe P to be measured by the non-contact type displacement gauge 2B, wherein that position corresponds to a position facing the center of the pipe P. Here, the non-contact type displacement gauge 2A may be located in the same manner as in the first embodiment.

The positioning controller 4 in the present embodiment predicts a time until a portion A1 of the pipe P whose displacement is measured by the non-contact type displacement gauge 2A reaches a predetermined position, for example, a position A3 after rotation by 180° on a straight line extending in the Z-axis direction through the rotational center of the pipe P on the basis of the positional relationship between the non-contact type displacement gauge 2A disposed in the Z-axis direction and the flaw detecting sensor 1, and the rotational speed of the pipe P. Thereafter, the positioning controller 4 controls the positioner 3A on the basis of the displacement measured by the non-contact type displacement gauge 2A and an operational delay time of the positioner 3 (specifically, the positioner 3A for moving the flaw detecting sensor 1 in the Z-axis direction) in such a manner that the flaw detecting sensor 1 in the Z-axis direction after the lapse of the predicted time is substantially constantly positioned relative to the pipe P after the lapse of the predicted time, and then, moves the flaw detecting sensor 1 in the Z-axis direction.

In the meantime, the positioning controller 4 predicts a time until a portion A2 of the pipe P whose displacement is measured by the non-contact type displacement gauge 2B reaches a predetermined position, for example, a position A4 after rotation by 180° on a straight line extending in the X-axis direction through the rotational center of the pipe P on the basis of the positional relationship between the non-contact type displacement gauge 2B disposed in the X-axis direction and the flaw detecting sensor 1, and the rotational speed of the pipe P. Thereafter, the positioning controller 4 controls the positioner 3B on the basis of the displacement measured by the non-contact type displacement gauge 2B and an operational delay time of the positioner 3 (specifically, the positioner 3B for moving the flaw detecting sensor 1 in the X-axis direction) in such a manner that the flaw detecting sensor 1 in the X-axis direction after the lapse of the predicted time is substantially constantly positioned relative to the pipe P after the lapse of the predicted time, and then, moves the flaw detecting sensor 1 in the X-axis direction.

As described above, in the tracking device 100A in the present embodiment, the flaw detecting sensor 1 is moved in the Z-axis direction on the basis of the displacement measured by the non-contact type displacement gauge 2A disposed in the Z-axis direction, and further, the flaw detecting sensor 1 is moved in the X-axis direction on the basis of the displacement measured by the non-contact type displacement gauge 2B disposed in the X-axis direction. In other words, the displacement measurement direction is coincident with the direction in which the flaw detecting sensor 1 is moved on the basis of the measured displacement, so that the flaw detecting sensor 1 is expected to more accurately track the pipe than that in the tracking device 100 in the first embodiment.

Third Embodiment

Figure 5:
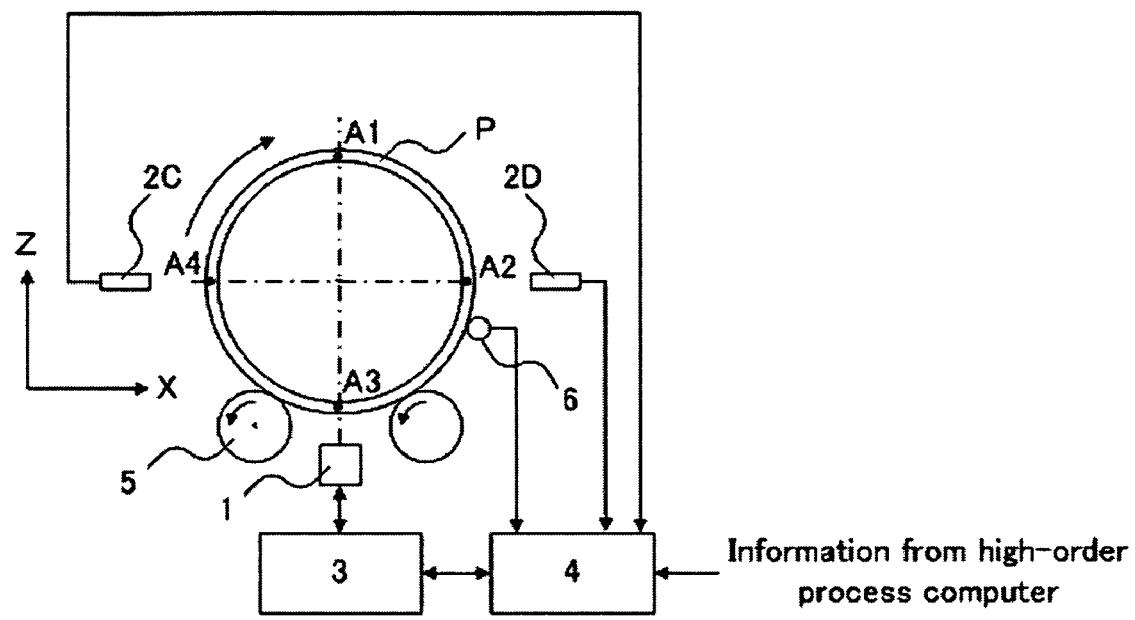
FIG. 5 is a front view schematically showing the configuration of a flaw detection tracking device for a pipe in a third embodiment according to the present invention.

FIG. 5 is a front view schematically showing the configuration of a flaw detection tracking device for a pipe in a third embodiment according to the present invention. As illustrated in FIG. 5, a tracking device 100B in the present embodiment is a device adapted to allow a flaw detecting sensor 1, which is disposed opposite to an outer surface of a pipe P and is relatively moved in the axial direction of the pipe P, to track the pipe P, so as to detect a flaw on the pipe P rotated in a circumferential direction, like in the first or second embodiment. Hereinafter, a description will be given on only points different from the first embodiment, and therefore, description on the same points will be omitted.

The tracking device 100B in the present embodiment includes a pair of non-contact type displacement gauges 2C and 2D arranged in an X-axis direction with the pipe P interposed therebetween. The non-contact type displacement gauges 2C and 2D may be fixed to, for example, an appropriate moving stage capable of moving the non-contact type displacement gauges 2C and 2D integrally with or independently of each other in a Z-axis direction, so that the non-contact type displacement gauges 2C and 2D are moved in the Z-axis direction in a state where the pipe P is mounted on turning rollers 5 in a stationary manner, wherein it is preferable that the pipe P should be formed into substantially a perfect circle in cross section in a direction perpendicular to an axial direction and almost without bend, thus positioning the non-contact type displacement gauges 2C and 2D at positions nearest to the pipe P to be measured by the non-contact type displacement gauges 2C and 2D, wherein that position corresponds to a position facing the center of the pipe P.

The positioning controller 4 in the present embodiment predicts a time until portions A4 and A2 of the pipe P whose displacement is measured by the pair of non-contact type displacement gauges 2C and 2D, reach predetermined positions, for example, the position A2 after rotation of the portion A4 by 180° and the position A4 after rotation of the portion A2 by 180°, on a straight line extending in the X-axis direction through the rotational center of the pipe P on the basis of the positional relationship between the pair of non-contact type displacement gauges 2C and 2D and the flaw detecting sensor 1, and the rotational speed of the pipe P. Thereafter, the positioning controller 4 controls a positioner 3B on the basis of a difference between the displacement measured by one non-contact type displacement gauge 2C and the displacement measured by the other non-contact type displacement gauge 2D and an operational delay time of a positioner 3 (specifically, the positioner 3B for moving the flaw detecting sensor 1 in the X-axis direction) in such a manner that the flaw detecting sensor 1 in the X-axis direction after the lapse of the predicted time is substantially constantly positioned relative to the pipe P after the lapse of the predicted time, and then, moves the flaw detecting sensor 1 in the X-axis direction.

The movement amount of the flaw detecting sensor 1 in the X-axis direction is expressed by, for example, Mx=(the displacement measured by the non-contact type displacement gauge 2C−the displacement measured by the non-contact type displacement gauge 2D)/2 rightward on the sheet of FIG. 5, or a value obtained by multiplying the amount Mx by a relaxation coefficient k, in which 0<k<1. This reason will be described below with reference to FIGS. 6A and 6B.

Figure 6A:
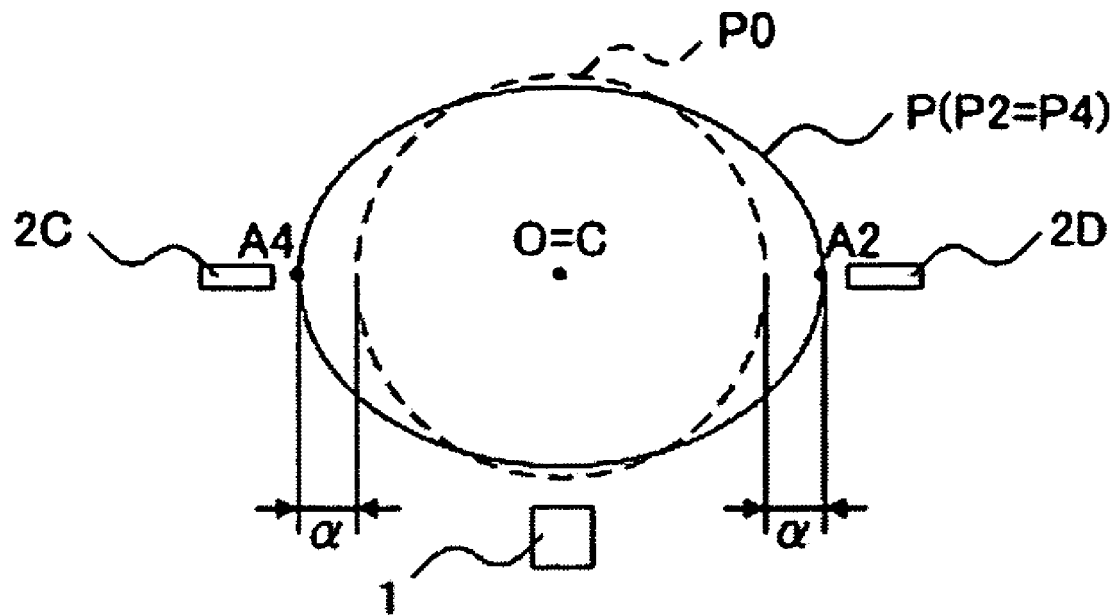
FIGS. 6A and 6B are diagrams illustrating the principle of the tracking device shown in FIG. 5.
Figure 6B:
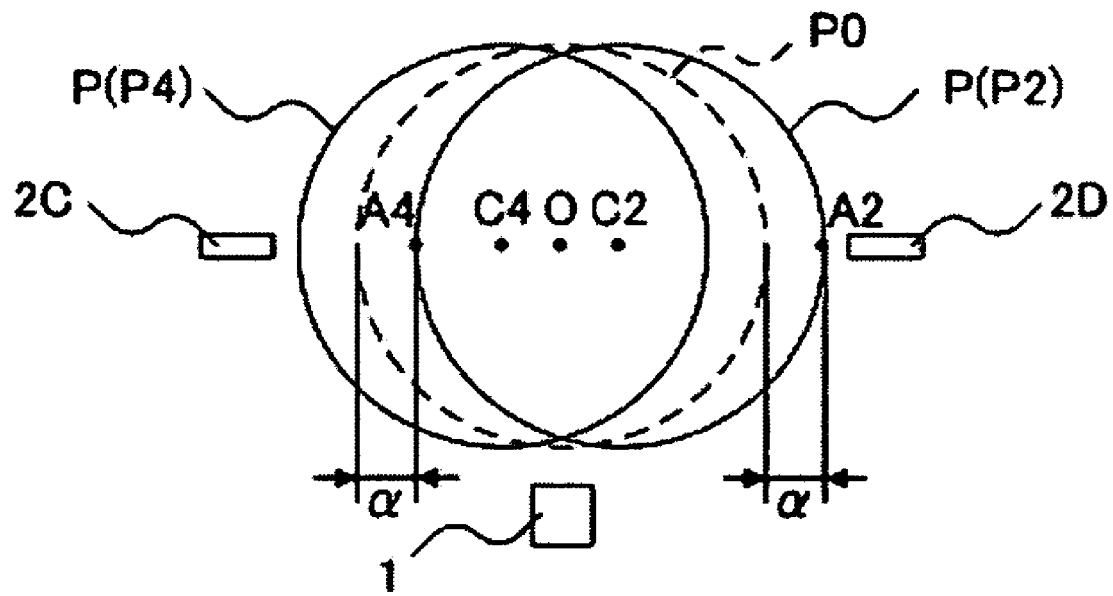

FIGS. 6A and 6B are diagrams illustrating the principle of the tracking device shown in the present embodiment. As illustrated in FIG. 6A, assume that a pipe P0 for use in setting the above-described positions of the non-contact type displacement gauges 2C and 2D is formed into a perfect circle in cross section in the direction perpendicular to the axial direction, that a center C of the pipe P0 is coincident with a rotational center O of the pipe P0, and that the distances up to the pipe P0 measured by the non-contact type displacement gauges 2C and 2D are referred to as references of the displacement, that is, origins of the non-contact type displacement gauges 2C and 2D. In the same manner, assume that the pipe P0 is used in setting the above-described initial position of the flaw detecting sensor 1, and that the initial position of the flaw detecting sensor 1 is set opposite to the center O of the pipe P0.

After the above-described initial setting, assume that the pipe P as a member whose flaw is to be actually detected, in which the center C of the pipe P is coincident with the rotational center O, like in the pipe P0 and a cross-sectional shape is an ellipse, is conveyed between the non-contact type displacement gauges 2C and 2D. As illustrated in FIG. 6A, elliptical long-diameter portions A4 and A2 face the non-contact type displacement gauges 2C and 2D, respectively, wherein the pipe P in this state is referred to as a pipe P2. Assume that when the pipe P2 is rotated by 180°, the portion A4 of the pipe P2 reaches a position facing the non-contact type displacement gauge 2D while the portion A2 of the pipe P2 reaches a position facing the non-contact type displacement gauge 2C, wherein the pipe P in this state is referred to as a pipe P4. During this rotation, since the center C of the pipe P is coincident with the rotational center O of the pipe P, it is unnecessary to move the flaw detecting sensor 1 in the X-axis direction. However, the displacement at the portion A4 of the pipe P2 measured by, for example, one non-contact type displacement gauge 2C becomes—α equal to the displacement when the center C of the pipe P2 is deviated from the rotational center O of the pipe P2. Therefore, if the movement amount of the flaw detecting sensor 1 in the X-axis direction is set in the state of the pipe P4 only by using the displacement—α, the flaw detecting sensor 1 is unfavorably moved even in the case where the center C of the pipe P is not deviated from the rotational center O of the pipe P, that is, where it is unnecessary to move the flaw detecting sensor 1 in the X-axis direction, thereby raising a problem of degradation of the tracking accuracy.

In contrast, like in the present embodiment, the movement amount of the flaw detecting sensor 1 in the X-axis direction in the state of the pipe P4 is set to Mx=(the displacement measured by the non-contact type displacement gauge 2C−the displacement measured by the non-contact type displacement gauge 2D)/2 rightward on the sheet of FIG. 5, as described above. As a consequence, the displacement at the portion A4 of the pipe P2 measured by the non-contact type displacement gauge 2C becomes—α, and further, the displacement at the portion A2 of the pipe P2 measured by the non-contact type displacement gauge 2D also becomes—α, whereby Mx=0. Thus, it is possible to maintain the tracking accuracy without moving the flaw detecting sensor 1 in the X-axis direction.

To the contrary, as illustrated in FIG. 6B, in the case where the pipe P as the member whose flaw is to be actually detected, has an outer diameter equal to that of the pipe P0 and is formed into a perfect circle in cross section, and further, the center of the pipe P is deviated from the rotational center O of the pipe P by a deviation amount α, the displacement at the portion A4 of the pipe P2 measured by the non-contact type displacement gauge 2C becomes α while the displacement at the portion A2 of the pipe P2 measured by the non-contact type displacement gauge 2D becomes—α, whereby Mx=α. When the pipe P2 is moved to the pipe P4 by the rotation by 180°, the displacement at a center C4 of the pipe P4 in the X-axis direction from the flaw detecting sensor 1 becomes—α, that is, the pipe P is moved by α leftward on the sheet of FIG. 6. As a consequence, the movement amount of the flaw detecting sensor 1 in the X-axis direction when the pipe P2 is moved to the pipe P4 after the rotation by 180° is set to Mx leftward on the sheet of FIG. 6, so that the position of the flaw detecting sensor 1 in the X-axis direction relative to the pipe P4 can be substantially constant, that is, substantially the same as the position of the flaw detecting sensor 1 in the X-axis direction relative to the pipe P0 at the initial position. In other words, the use of Mx as the movement amount of the flaw detecting sensor 1 in the X-axis direction is effective in not only the pipe P formed into an ellipse in cross section, as shown in FIG. 6A, but also the bending pipe P having its center deviated from its rotational center O, as shown in FIG. 6B. Here, in order to avoid the problem of degradation of the tracking accuracy, it is preferable that a value obtained by multiplying Mx by a predetermined relaxation coefficient k, wherein 0<k<1, should be set as the movement amount of the flaw detecting sensor 1, as described in the first embodiment.

A positioning controller 4 in the present embodiment predicts a time until the portion A4 or A2 of the pipe P whose displacement is measured by either one selected from the non-contact type displacement gauges 2C and 2D reaches a predetermined position, for example, the position A1 after rotation of the portion A4 by 90° or the position A3 after rotation of the portion A2 by 90°, on a straight line extending in the Z-axis direction through the rotational center of the pipe P on the basis of the positional relationship between the selected non-contact type displacement gauge 2C or 2D and the flaw detecting sensor 1, and the rotational speed of the pipe P. Thereafter, the positioning controller 4 controls the positioner 3A on the basis of the displacement measured by the selected non-contact type displacement gauge and an operational delay time of a positioner 3 (specifically, the positioner 3A for moving the flaw detecting sensor 1 in the Z-axis direction) in such a manner that the flaw detecting sensor 1 in the Z-axis direction after the lapse of the predicted time is substantially constantly positioned relative to the pipe P after the lapse of the predicted time, and then, moves the flaw detecting sensor 1 in the Z-axis direction.

The positioning controller 4 in the present embodiment is configured in a favorable modification such that the outer diameter of the pipe P can be calculated on the basis of the displacement measured by the pair of non-contact type displacement gauges 2C and 2D. Specifically, the outer diameter of the pipe P can be calculated by subtracting each of distances up to the pipe P measured by the non-contact type displacement gauges 2C and 2D from a separation distance between the non-contact type displacement gauges 2C and 2D. As described above, the non-contact type displacement gauges 2C and 2D are positioned in such a manner as to face each other in the X-axis direction with the center of the pipe P0 for the initial setting interposed therebetween. Here, if the center of the pipe P is deviated toward the Z-axis direction from the facing direction between the non-contact type displacement gauges 2C and 2D, that is, a straight line connecting the non-contact type displacement gauges 2C and 2D caused by a positional fluctuation in the Z-axis direction such as a bend in the pipe P whose outer diameter is to be actually measured, an error according to the above-described deviation geometrically occurs in the measured outer diameter of the pipe P calculated in the above-described manner. Specifically, as the above-described deviation becomes larger, the measured outer diameter of the pipe P becomes smaller than the actual outer diameter of the pipe P. In the meantime, if the above-described deviation is invariable, the error geometrically becomes larger as the actual outer diameter of the pipe P becomes smaller. In view of this, in order to keep the outer diameter measuring accuracy in spite of the bend occurring in the pipe P, it is preferable to correct the obtained outer diameter measurement value, for example, to add a predetermined correction value according to the above-described deviation and an approximate outer diameter such as a design value of the pipe P.

The above-described correction can be carried out in a manner, for example, as described below. First, the positioning controller 4 is so configured as to store the outer diameter measurement value and the position of the flaw detecting sensor 1 in the Z-axis direction in time series with respect to a single pipe P. Moreover, the positioning controller 4 previously stores therein the outer diameter design value of the pipe P. In addition, the positioning controller 4 previously stores therein a correction value to be added to the outer diameter measurement value with respect to each of the above-described deviation from the center of the pipe P and the outer diameter design value of the pipe P in the form of, for example, a table. Here, the position of the flaw detecting sensor 1 in the Z-axis direction at a certain timing corresponds to the above-described deviation from the center of the pipe P at the same timing when the tracking accuracy of the flaw detecting sensor 1 is high. As a consequence, the above-described deviation from the center of the pipe P at the same timing can be calculated on the basis of the position of the flaw detecting sensor 1 in the Z-axis direction at each timing stored in the positioning controller 4. The positioning controller 4 calculates the deviation from the center of the pipe P at each timing on the basis of the position of the flaw detecting sensor 1 in the Z-axis direction at each timing stored therein, sequentially selects a correction value according to the calculated deviation and the inputted outer diameter design value of the pipe P from the table, and adds the correction value to the stored outer diameter measurement value at the same timing. Thus, the correction of the stored outer diameter measurement value at each timing in the above-described manner enables the outer diameter measuring accuracy to be kept even with the positional fluctuation of the pipe P in the Z-axis direction such as a bend.

Subsequently, the feature according to the present invention will be further clarified by describing examples and comparative examples.

Example 1-1

A tracking accuracy evaluation test on the flaw detecting sensor 1 was conducted by using the tracking device 100B illustrated in FIG. 5, that is, the above-described configuration in the third embodiment. As the member whose flaw is to be detected, used was a pipe whose outer diameter is 73 mm in design value and whose deviation of the center of the pipe from the rotational center of the pipe caused by a bend is about ±3 mm (hereinafter referred to as "a bent pipe"). The bent pipe was mounted on the turning rollers 5, and then, was not conveyed in the axial direction but rotated in the circumferential direction (at a rotational speed of 180 rpm). Thereafter, the rotated bent pipe was tracked by the flaw detecting sensor 1, as described below.

(1) Tracking by Flaw Detecting Sensor 1 in X-Axis Direction

The time until the portions of the bent pipe whose displacement was measured by the non-contact type displacement gauges 2C and 2D, respectively, reached the positions after the rotation by 180° was predicted on the basis of the positional relationship between the non-contact type displacement gauges 2C and 2D and the flaw detecting sensor 1 and the rotational speed of the bent pipe. Thereafter, the positioner 3B was controlled on the basis of the difference between the displacement measured by the non-contact type displacement gauge 2C and the displacement measured by the non-contact type displacement gauge 2D and the operational delay time of the positioner 3B in such a manner that the flaw detecting sensor 1 in the X-axis direction after the lapse of the predicted time was substantially constantly positioned relative to the bent pipe after the lapse of the predicted time, and then, the flaw detecting sensor 1 was moved in the X-axis direction. The movement amount Mx of the flaw detecting sensor 1 in the X-axis direction was equal to (the displacement measured by the non-contact type displacement gauge 2C–the displacement measured by the non-contact type displacement gauge 2D)/2.

(2) Tracking by Flaw Detecting Sensor 1 in Z-Axis Direction

The time until the portion of the bent pipe whose displacement was measured by the non-contact type displacement gauge 2D reached the position after the rotation by 90° was predicted on the basis of the positional relationship between the non-contact type displacement gauge 2D and the flaw detecting sensor 1 and the rotational speed of the bent pipe. Thereafter, the positioner 3A was controlled on the basis of the displacement measured by the non-contact type displacement gauge 2D and the operational delay time of the positioner 3A in such a manner that the flaw detecting sensor 1 in the Z-axis direction after the lapse of the predicted time was substantially constantly positioned relative to the bent pipe after the lapse of the predicted time, and then, the flaw detecting sensor 1 was moved in the Z-axis direction.

Example 1-2

The tracking accuracy evaluation test on the flaw detecting sensor 1 was conducted under the same conditions as in Example 1-1 except for the use of only the displacement measured by the non-contact type displacement gauge 2D, that is, without using the displacement measured by the non-contact type displacement gauge 2C in order to allow the flaw detecting sensor 1 to track the bent pipe. Specifically, the flaw detecting sensor 1 was allowed to track the bent pipe in a manner described below.

(1) Tracking by Flaw Detecting Sensor 1 in X-Axis Direction

The time until the portion of the bent pipe whose displacement was measured by the non-contact type displacement gauge 2D reached the position after the rotation by 180° was predicted on the basis of the positional relationship between the non-contact type displacement gauge 2D and the flaw detecting sensor 1 and the rotational speed of the bent pipe. Thereafter, the positioner 3B was controlled on the basis of the displacement measured by the non-contact type displacement gauge 2D and the operational delay time of the positioner 3B in such a manner that the flaw detecting sensor 1 in the X-axis direction after the lapse of the predicted time was substantially constantly positioned relative to the bent pipe after the lapse of the predicted time, and then, the flaw detecting sensor 1 was moved in the X-axis direction.

(2) Tracking by Flaw Detecting Sensor 1 in Z-Axis Direction

The flaw detecting sensor 1 tracked the bent pipe in the same manner as in Example 1-1.

Comparative Example 1

A test was conducted under the same conditions as in Example 1-1 except that the flaw detecting sensor 1 did not track the bent pipe, that is, the flaw detecting sensor 1 remained fixed at the initial position.
<Method for Evaluating Tracking Accuracy>

(1) Method for Evaluating Tracking Accuracy in Z-Axis Direction

A micrometer serving as a contact type displacement gauge, that is, a Z-axis contact type displacement gauge was attached to the flaw detecting sensor 1, and then, its probe was brought into contact with the bottom surface of the bent pipe. Displacement of the probe of the micrometer was measured in each of Examples 1-1 and 1-2 and Comparative Example 1. When the flaw detecting sensor 1 completely tracks the positional fluctuation of the bent pipe in the Z-axis direction according to the rotation in the circumferential direction, the above-described measured displacement shall become constant all the time in principle. As a consequence, it was evaluated that the tracking accuracy in the Z-axis direction was higher as the fluctuation width of the displacement measured by the Z-axis contact type displacement gauge was smaller.

(2) Method for Evaluating Tracking Accuracy in X-Axis Direction

A micrometer serving as a contact type displacement gauge, that is, a X-axis contact type displacement gauge was attached to the flaw detecting sensor 1, and then, its probe was brought into contact with the side surface of the bent pipe in the X-axis direction. Displacement of the probe of the micrometer was measured in each of Examples 1-1 and 1-2 and Comparative Example 1. When the flaw detecting sensor 1 completely tracks the positional fluctuation of the bent pipe in the X-axis direction according to the rotation in the circumferential direction, the above-described measured displacement shall become constant all the time in principle. As a consequence, it was evaluated that the tracking accuracy in the X-axis direction was higher as the fluctuation width of the displacement measured by the X-axis contact type displacement gauge was smaller.
<Evaluation Results of Tracking Accuracy>

Figure 7A:
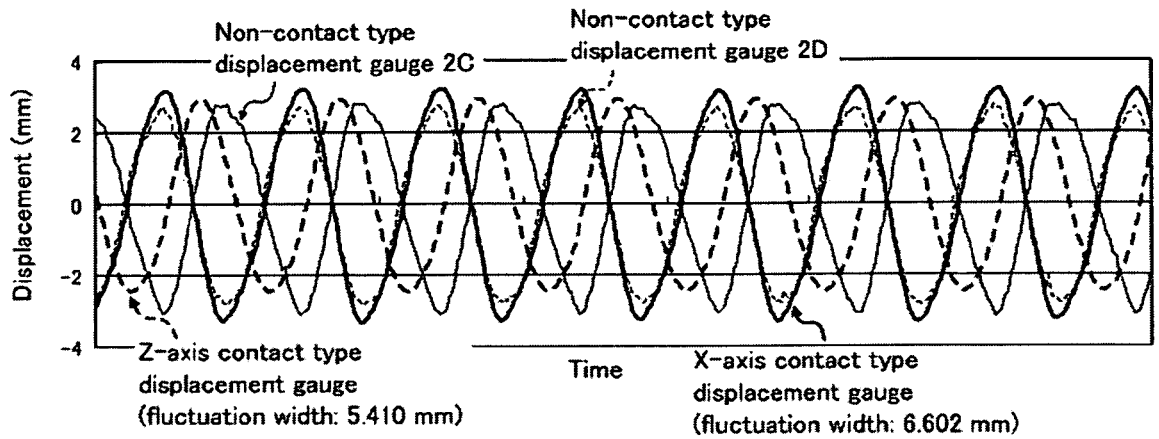
FIGS. 7A, 7B and 7C are graphs illustrating one example of evaluation results of tracking accuracy in examples according to the present invention and a comparative example.
Figure 7B:
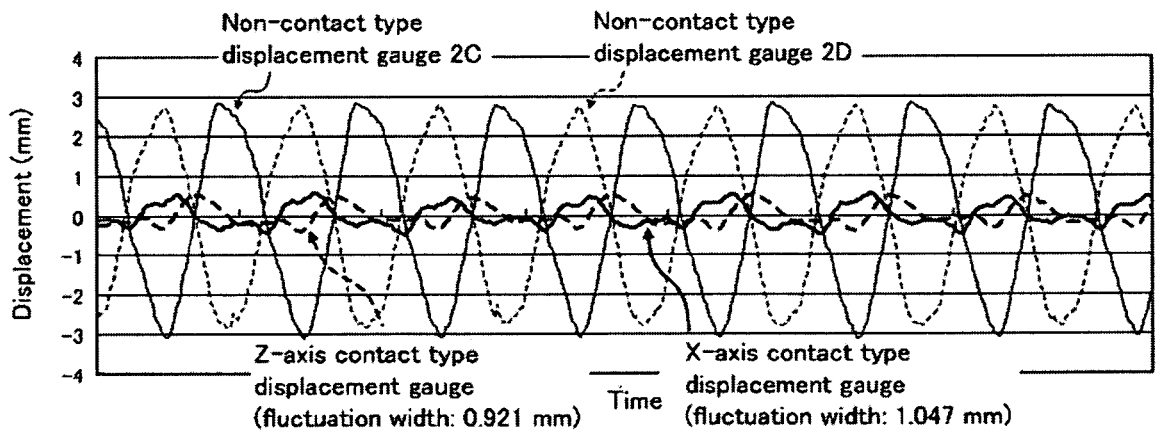
Figure 7C:
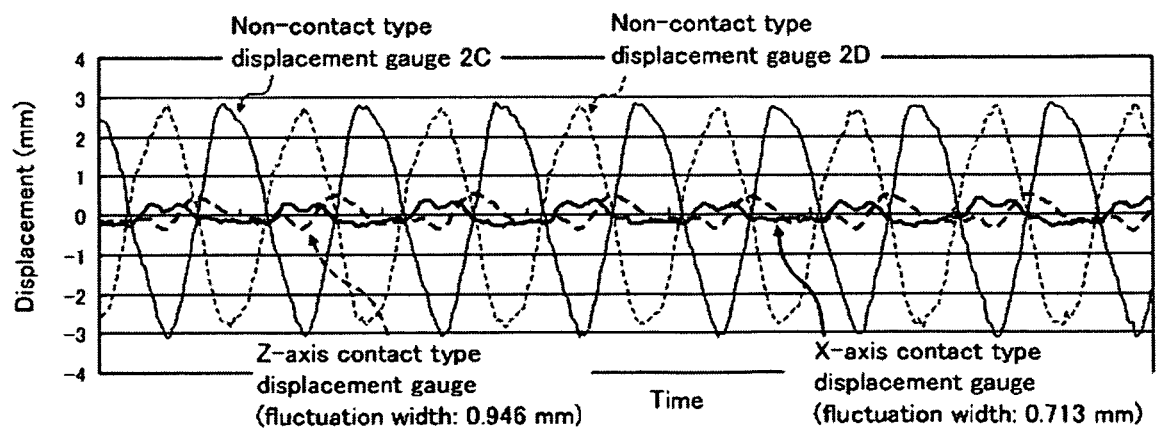

FIGS. 7A, 7B and 7C are graphs illustrating the above-described evaluation results of the tracking accuracy, wherein FIG. 7A illustrates the results of Comparative Example 1; FIG. 7B illustrates the results of Example 1-2; and FIG. 7C illustrates the results of Example 1-1. The displacement amounts measured by the non-contact type displacement gauges 2C and 2D also are plotted in the graphs of FIGS. 7A, 7B and 7C in addition to the displacement amounts measured by the Z-axis contact type displacement gauge and the X-axis contact type displacement gauge.

As illustrated in FIGS. 7A, 7B and 7C, the fluctuation width of the displacement measured by the Z-axis contact type displacement gauge in a graph indicated by a bold broken line was 5.410 mm in Comparative Example 1 (FIG. 7A). In contrast, it was 0.946 mm in Example 1-1 (FIG. 7C) and 0.921 mm in Example 1-2 (FIG. 7B), respectively. As a result, it was found that the tracking accuracy in the Z-axis direction was remarkably higher in Examples than in Comparative Example.

In the meantime, as illustrated in FIGS. 7A, 7B and 7C, the fluctuation width of the displacement measured by the X-axis contact type displacement gauge in a graph indicated by a bold solid line was 6.602 mm in Comparative Example 1 (FIG. 7A). In contrast, it was 0.713 mm in Example 1-1 (FIG. 7C) and 1.047 mm in Example 1-2 (FIG. 7B), respectively. As a result, it was found that the tracking accuracy in the X-axis direction was remarkably higher in Examples than in Comparative Example. Here, comparing Example 1-1 with Example 1-2, the reason why the fluctuation width of the displacement in Example 1-1 was smaller was that the bent pipe was not a perfect circle in cross section but slightly included an elliptical component. In other words, it is construed that the effective function of the configuration in Example 1-1, that is, the configuration in the above-described third embodiment can reduce the adverse influence by the elliptical component, thus enhancing the tracking accuracy.

Example 2-1

A tracking accuracy evaluation test on the flaw detecting sensor 1 was conducted under the same conditions as in Example 1-1 except that as the member whose flaw is to be detected, used was a pipe whose outer diameter is 73 mm in design value and which is formed into an ellipse in cross section having an ellipticity of 2.7% (hereinafter referred to as "an elliptic pipe"). Here, the ellipticity is defined by the following expression: ellipticity=2×(greatest outer diameter−smallest outer diameter)/(greatest outer diameter+smallest outer diameter)×100%.

Example 2-2

A tracking accuracy evaluation test on the flaw detecting sensor 1 was conducted under the same conditions as in Example 1-2 except that as the member whose flaw is to be detected, used was an elliptic pipe.

Comparative Example 2

A test was conducted under the same conditions as in Comparative Example 1 except that as the member whose flaw is to be detected, used was an elliptic pipe.
<Method for Evaluating Tracking Accuracy>
(1) Method for Evaluating Tracking Accuracy in Z-Axis Direction The tracking accuracy in the Z-axis direction was evaluated in Examples 2-1 and 2-2 and Comparative Example 2 by the same evaluating method as Examples 1-1 and 1-2 and Comparative Example 1.

(2) Method for Evaluating Tracking Accuracy in X-Axis Direction

Even if the value measured by each of the non-contact type displacement gauges is fluctuated according to the rotation of the elliptic pipe, the flaw detecting sensor 1 need not be moved in the X-axis direction as long as the center of the elliptic pipe is not deviated from the rotational center of the elliptic pipe. To the contrary, the movement of the flaw detecting sensor 1 in the X-axis direction signifies a low tracking accuracy. Therefore, the displacement of the piston rod 311 in the positioner 3B (see FIG. 2) corresponding to the movement of the flaw detecting sensor 1 in the X-axis direction was measured herein. As the fluctuation width of the measured displacement was smaller, it was evaluated that the tracking accuracy was higher. Specifically, a probe of a micrometer serving as a contact type displacement gauge, that is, an X-axis contact type displacement gauge was brought into contact with the end face of the piston rod 311. Displacement of the probe of the micrometer was measured in each of Examples 2-1 and 2-2 and Comparative Example 2. As described above, it was evaluated that the tracking accuracy in the X-axis direction was higher as the fluctuation width of the displacement measured by the X-axis contact type displacement gauge was smaller.
<Evaluation Results of Tracking Accuracy>

Figure 8A:
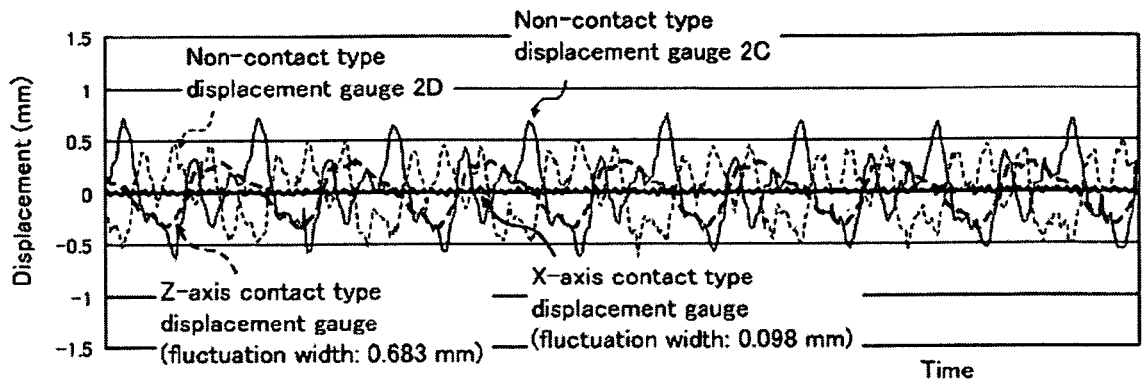
FIGS. 8A, 8B and 8C are graphs illustrating another example of evaluation results of the tracking accuracy in examples according to the present invention and a comparative example.
Figure 8B:
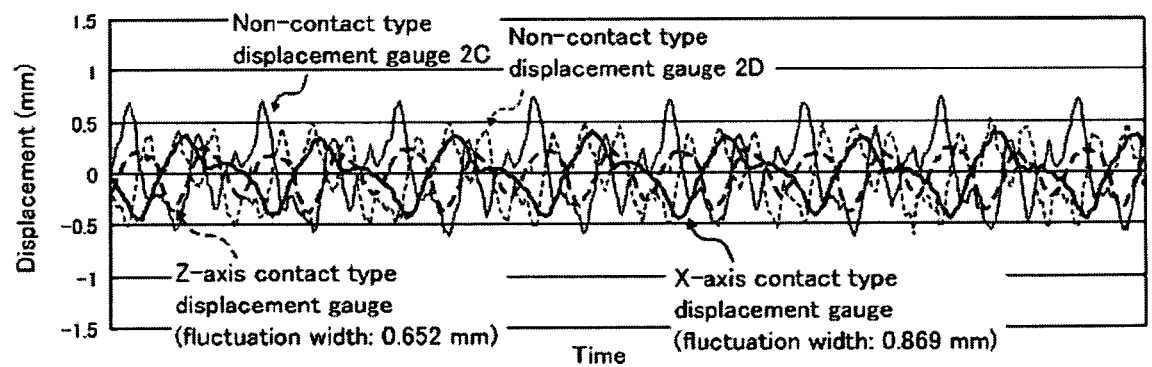
Figure 8C:
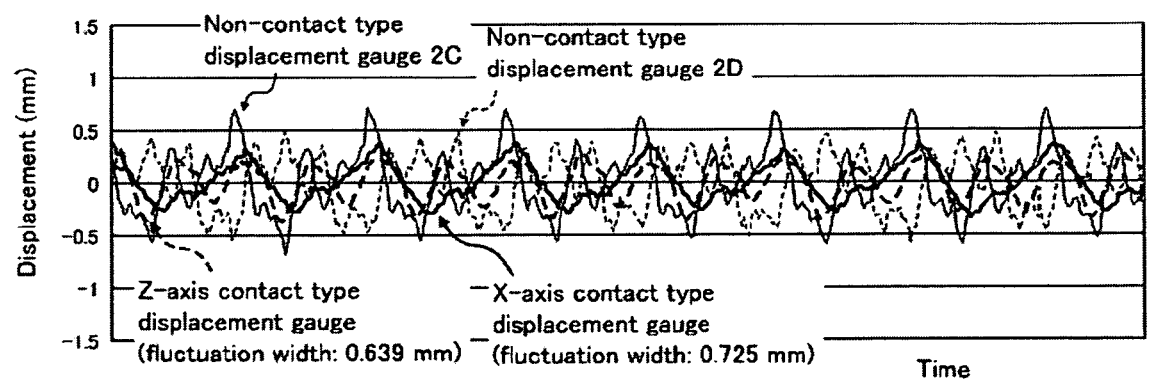

FIGS. 8A, 8B and 8C are graphs illustrating the above-described evaluation results of the tracking accuracy, wherein FIG. 8A illustrates the results of Comparative Example 2; FIG. 8B illustrates the results of Example 2-2; and FIG. 8C illustrates the results of Example 2-1. The displacement amounts measured by the non-contact type displacement gauges 2C and 2D also are plotted in the graphs of FIGS. 8A, 8B and 8C in addition to the displacement amounts measured by the Z-axis contact type displacement gauge and the X-axis contact type displacement gauge.

As illustrated in FIGS. 8A, 8B and 8C, the fluctuation width of the displacement measured by the Z-axis contact type displacement gauge in a graph indicated by a bold broken line was 0.683 mm in Comparative Example 2 (FIG. 8A).

In contrast, it was 0.639 mm in Example 2-1 (FIG. 8C) and 0.652 mm in Example 2-2 (FIG. 8B), respectively. As a result, it was found that the tracking accuracy in the Z-axis direction was slightly higher in Examples than in Comparative Example.

In the meantime, as illustrated in FIGS. 8A, 8B and 8C, the fluctuation width of the displacement measured by the X-axis contact type displacement gauge in a graph indicated by a bold solid line was 0.098 mm in Comparative Example 2 (FIG. 8A). In contrast, it was 0.725 mm in Example 2-1 (FIG. 8C) and 0.869 mm in Example 2-2 (FIG. 8B), respectively. Here, the fluctuation width of the displacement measured by the X-axis contact type displacement gauge in Comparative Example 2 naturally approached 0 mm since the flaw detecting sensor 1 was fixedly positioned (the fluctuation of the displacement was slightly caused by a mechanical vibration). As a result, Examples could not be compared with Comparative Example regarding to the tracking accuracy in the X-axis direction. Comparing Example 2-1 with Example 2-2, it was found that the tracking accuracy was enhanced in Example 2-1 since the fluctuation width of the displacement in Example 2-1 was smaller than in Example 2-2, as described above. This result revealed that the configuration of the above-described third embodiment out of the preferred embodiments according to the present invention was particularly effective in allowing the flaw detecting sensor 1 to track the pipe formed into an ellipse in cross section.

What is claimed is:

1. A flaw detecting tracking device for a pipe or tube, by which a flaw detecting sensor disposed opposite to an outer surface of a pipe or tube and relatively moving along an axial direction of the pipe or tube, for detecting a flaw on the pipe or tube rotated in a circumferential direction, tracks the pipe or tube, the tracking device comprising:
   at least one non-contact type displacement gauge for measuring displacement at the outer surface of the pipe or tube in a non-contact state;
   a positioner for moving the flaw detecting sensor within a plane perpendicular to an axial direction of the pipe or tube along the opposite direction of the pipe or tube to the flaw detecting sensor and a direction perpendicular to the opposite direction; and
   a positioning controller for controlling the positioner,
   the positioning controller predicting a time until a portion of the pipe or tube whose displacement is measured by the non-contact type displacement gauge reaches a predetermined position on a straight line extending in the opposite direction through the rotational center of the pipe or tube on the basis of the positional relationship between the non-contact type displacement gauge and the flaw detecting sensor and a rotational speed of the pipe or tube; controlling the positioner on the basis of the displacement measured by the non-contact type displacement gauge and an operational delay time of the positioner in such a manner that the relative position of the flaw detecting sensor after the lapse of the predicted time to the pipe or tube after the lapse of the predicted time becomes substantially constant in the opposite direction; and moving the flaw detecting sensor along the opposite direction, and
   the positioning controller predicting a time until a portion of the pipe or tube whose displacement is measured by the non-contact type displacement gauge reaches a predetermined position on a straight line extending in the perpendicular direction through the rotational center of the pipe or tube on the basis of the positional relationship between the non-contact type displacement gauge and the flaw detecting sensor and a rotational speed of the pipe or tube; controlling the positioner on the basis of the displacement measured by the non-contact type displacement gauge and an operational delay time of the positioner in such a manner that the relative position of the flaw detecting sensor after the lapse of the predicted time to the pipe or tube after the lapse of the predicted time becomes substantially constant in the perpendicular direction; and moving the flaw detecting sensor along the perpendicular direction.

2. The flaw detecting tracking device for a pipe or tube according to claim 1, further comprising:

at least two non-contact type displacement gauges disposed along the opposite direction and the perpendicular direction, respectively, wherein the positioning controller predicts a time until a portion of the pipe or tube whose displacement is measured by the non-contact type displacement gauge disposed along the opposite direction reaches a predetermined position on a straight line extending in the opposite direction through the rotational center of the pipe or tube on the basis of the positional relationship between the non-contact type displacement gauge disposed along the opposite direction and the flaw detecting sensor and a rotational speed of the pipe or tube, controls the positioner on the basis of the displacement measured by the non-contact type displacement gauge disposed along the opposite direction and an operational delay time of the positioner in such a manner that the relative position of the flaw detecting sensor after the lapse of the predicted time to the pipe or tube after the lapse of the predicted time becomes substantially constant in the opposite direction, and moves the flaw detecting sensor along the opposite direction, and the positioning controller predicts a time until a portion of the pipe or tube whose displacement is measured by the non-contact type displacement gauge disposed along the perpendicular direction reaches a predetermined position on a straight line extending in the perpendicular direction through the rotational center of the pipe or tube on the basis of the positional relationship between the non-contact type displacement gauge disposed along the perpendicular direction and the flaw detecting sensor and a rotational speed of the pipe or tube, controls the positioner on the basis of the displacement measured by the non-contact type displacement gauge disposed along the perpendicular direction and an operational delay time of the positioner in such a manner that the relative position of the flaw detecting sensor after the lapse of the predicted time to the pipe or tube after the lapse of the predicted time becomes substantially constant in the perpendicular direction, and moves the flaw detecting sensor along the perpendicular direction.

3. The flaw detecting tracking device for a pipe or tube according to claim 1, further comprising:

a pair of non-contact type displacement gauges disposed opposite to each other in the perpendicular direction with a pipe or tube interposed therebetween, wherein the positioning controller predicts a time until a portion of the pipe or tube whose displacement is measured by the pair of non-contact type displacement gauges reaches a predetermined position on a straight line extending in the perpendicular direction through the rotational center of the pipe or tube on the basis of the positional relationship between the pair of non-contact type displacement gauges and the flaw detecting sensor and a rotational speed of the pipe or tube, controls the positioner on the basis of a difference between displacement measured by one of the non-contact type displacement gauges and displacement measured by the other non-contact type displacement gauge and an operational delay time of the positioner in such a manner that the relative position of the flaw detecting sensor after the lapse of the predicted time to the pipe or tube after the lapse of the predicted time becomes substantially constant in the perpendicular direction, and moves the flaw detecting sensor along the perpendicular direction, and the positioning controller predicts a time until a portion of the pipe or tube whose displacement is measured by any one selected from among the pair of non-contact type displacement gauges and the other non-contact type displacement gauge reaches a predetermined position on a straight line extending in the opposite direction through the rotational center of the pipe or tube on the basis of the positional relationship between the selected non-contact type displacement gauge and the flaw detecting sensor and a rotational speed of the pipe or tube, controls the positioner on the basis of displacement measured by the selected non-contact type displacement gauge and an operational delay time of the positioner in such a manner that the relative position of the flaw detecting sensor after the lapse of the predicted time to the pipe or tube after the lapse of the predicted time becomes substantially constant in the opposite direction, and moves the flaw detecting sensor along the opposite direction.

4. The flaw detecting tracking device for a pipe or tube according to claim 3, wherein the positioning controller calculates an outer diameter of the pipe or tube on the basis of the displacements measured by the pair of non-contact type displacement gauges.

5. The flaw detecting tracking device for a pipe or tube according to claim 1, wherein the non-contact type displacement gauge is an eddy current type displacement gauge, and the positioning controller corrects the displacement measured by the non-contact type displacement gauge according to a material of the pipe or tube, to control the positioner on the basis of the corrected displacement.

6. The flaw detecting tracking device for a pipe or tube according to claim 1, wherein the flaw detecting sensor is an ultrasonic probe, and the positioning controller controls the positioner with respect to the pipe or tube in a stationary state, moves the ultrasonic probe along the perpendicular direction, and sets, as an initial position of the ultrasonic probe, a position at which an echo intensity received from the outer surface of the pipe or tube by the ultrasonic probe becomes highest.

7. An automatic flaw detecting apparatus for a pipe or tube comprising:

the flaw detection tracking device for the pipe or tube according to claim 1; and a flaw detecting sensor for tracking the pipe or tube by the flaw detection tracking device for the pipe or tube.

* * * * *